(12) United States Patent
Kamaguchi et al.

(10) Patent No.: US 9,510,609 B2
(45) Date of Patent: Dec. 6, 2016

(54) SEAMLESS CAPSULE AND MANUFACTURING METHOD THEREFOR

(71) Applicant: MORISHITA JINTAN CO., LTD., Osaka-shi, Osaka (JP)

(72) Inventors: Ryosei Kamaguchi, Hirakata (JP); Osami Nakano, Hirakata (JP); Hisaaki Hatanaka, Hirakata (JP)

(73) Assignee: MORISHITA JINTAN CO., LTD., Osaka (JP)

( * ) Notice: Subject to any disclaimer, the term of this patent is extended or adjusted under 35 U.S.C. 154(b) by 0 days.

(21) Appl. No.: 14/347,869

(22) PCT Filed: Sep. 21, 2012

(86) PCT No.: PCT/JP2012/074246
§ 371 (c)(1),
(2) Date: Mar. 27, 2014

(87) PCT Pub. No.: WO2013/047376
PCT Pub. Date: Apr. 4, 2013

(65) Prior Publication Data
US 2014/0234411 A1  Aug. 21, 2014

(30) Foreign Application Priority Data
Sep. 29, 2011  (JP) .................................. 2011-214543

(51) Int. Cl.
| | | |
|---|---|---|
| *A23L 1/00* | (2006.01) |
| *A61J 1/00* | (2006.01) |
| *A61K 9/48* | (2006.01) |
| *A61K 9/50* | (2006.01) |
| *B01J 13/04* | (2006.01) |
| *A61K 9/00* | (2006.01) |

(52) U.S. Cl.
CPC .............. *A23L 1/0029* (2013.01); *A23L 27/72* (2016.08); *A23P 10/30* (2016.08); *A61J 1/00* (2013.01); *A61K 9/0056* (2013.01); *A61K 9/4825* (2013.01); *A61K 9/4833* (2013.01); *A61K 9/5015* (2013.01); *A61K 9/5057* (2013.01); *A61K 9/5089* (2013.01); *B01J 13/04* (2013.01)

(58) Field of Classification Search
CPC ....................................................... A23P 10/30
See application file for complete search history.

(56) References Cited

U.S. PATENT DOCUMENTS 5,254,294 A * 10/1993 Wunderlich et al. .............. 264/4
5,330,835 A *  7/1994 Kikuchi et al. .......... 428/402.22
5,603,952 A    2/1997 Soper
(Continued)

FOREIGN PATENT DOCUMENTS

CN      101969932 A      2/2011
EP      0 116 311        8/1984
(Continued)

*Primary Examiner* — Ileana Popa
*Assistant Examiner* — Nicole Babson
(74) *Attorney, Agent, or Firm* — Hamre, Schumann, Mueller & Larson, P.C.

(57) ABSTRACT

The present invention is related to a seamless capsule which easily dissolves in the oral cavity etc. The present invention provides a seamless capsule comprising a capsule content solution, and a capsule shell enclosing the capsule content solution, wherein the capsule shell comprises a gelatin having a bloom value of 50 to 190 and wherein the seamless capsule has a capsule shell-dissolution time of 60 seconds or less when the dissolution time is determined by a disintegration test using water as a test solution.

3 Claims, 1 Drawing Sheet

(56) References Cited

U.S. PATENT DOCUMENTS

| | | |
|---|---|---|
| 5,780,056 A | 7/1998 | Akamatsu et al. |
| 6,258,380 B1 | 7/2001 | Overholt |
| 2005/0079215 A1 | 4/2005 | Schleifenbaum et al. |
| 2005/0100593 A1 | 5/2005 | Furuta |
| 2005/0169983 A1 | 8/2005 | Hassan et al. |
| 2010/0178335 A1 | 7/2010 | Echanagorria et al. |
| 2010/0285121 A1 | 11/2010 | Uchiyama et al. |

FOREIGN PATENT DOCUMENTS

| | | |
|---|---|---|
| EP | 1 447 082 | 8/2004 |
| EP | 2 172 225 | 4/2010 |
| JP | 55-91358 | 7/1980 |
| JP | 7-502912 | 3/1995 |
| JP | 10-273436 | 10/1998 |
| JP | 10-512141 | 11/1998 |
| JP | 2001-89362 | 4/2001 |
| JP | 2004-196706 | 7/2004 |
| JP | 2005-139152 | 6/2005 |
| JP | 2005-529128 | 9/2005 |
| JP | 2006-512944 | 4/2006 |
| JP | 2010-501632 | 1/2010 |
| JP | 2010-260812 | 11/2010 |
| WO | WO 00/51574 | 9/2000 |

* cited by examiner

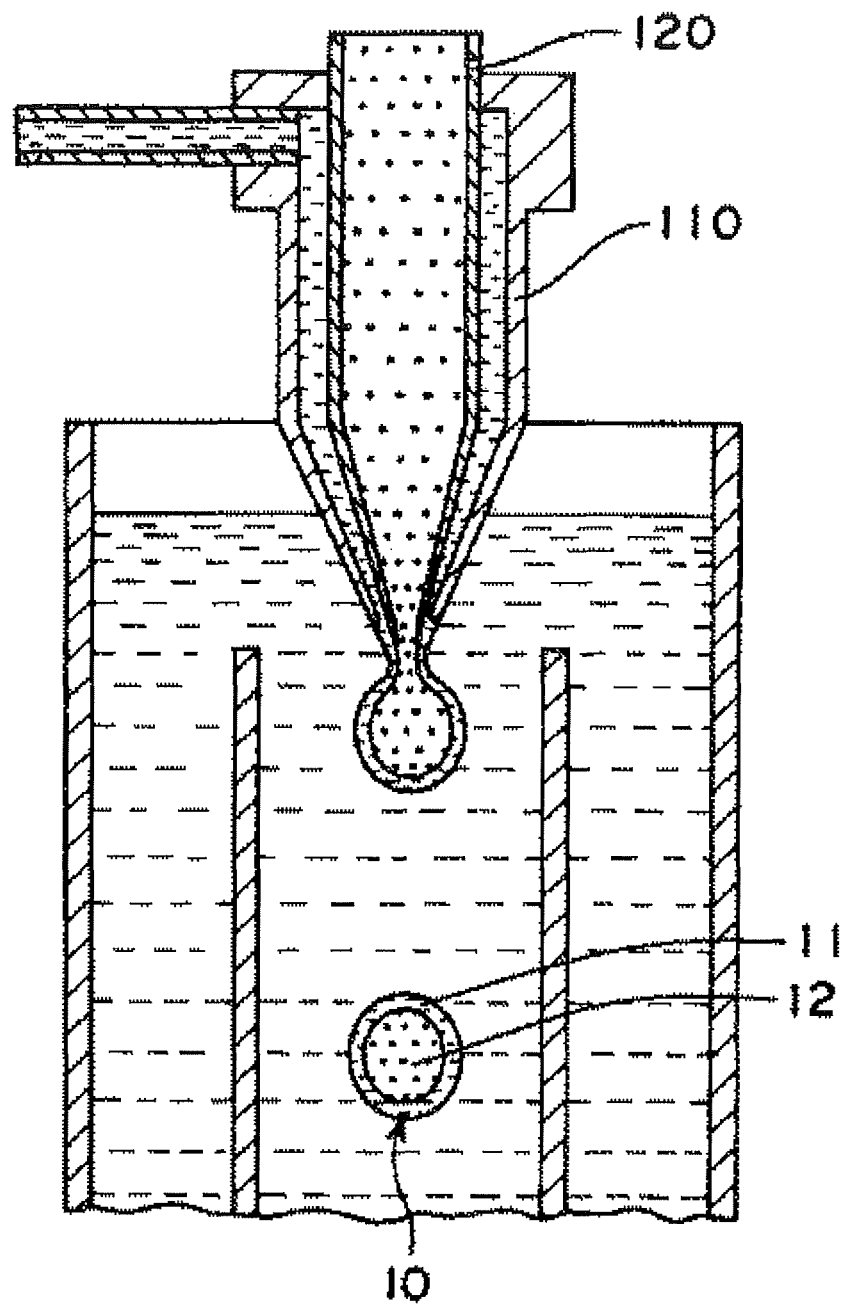

SEAMLESS CAPSULE AND MANUFACTURING METHOD THEREFOR

TECHNICAL FIELD

The present invention is related to a seamless capsule which easily dissolves in the oral cavity etc.

BACKGROUND ART

Capsules enclosing various medicines, food, favorite item or the like are widely employed, because one takes capsules easily. In the capsules, seamless capsule are generally used for encapsulating liquid content, because of high productivity. An example of such seamless capsules includes seamless capsules for favorite item or oral care.

In the seamless capsule, a capsule shell has function of a container of a capsule content solution. The capsule shell, accordingly, has strength enough to keep maintaining capsule content solution, when producing seamless capsules. On the other hand, seamless capsules enclosing favorite item or oral care material are desired to smoothly and easily dissolve in the oral cavity, when one takes in them. In the case where capsule shell does not dissolve easily in the oral cavity, the capsule shell remains in the oral cavity and the remaining brings unpleasant feeling like eating rubber.

Accordingly, seamless capsules should have enough strength when producing them and should easily dissolve in the oral cavity when one takes them, which are to be inconsistent properties. It, however, has been difficult that these properties are consistent to a high degree.

JP 2006-512944 A (Patent Literature 1) discloses a spherical capsule comprising a liquid core and a seamless solid shell enclosing the liquid core, wherein the capsule has a diameter of 4 to 8 mm, has a shell thickness of 20 to 200 μm and a ratio of shell thickness and capsule diameter of 0.004 to 0.04, the shell contains a gelatin of 70 to 90% by mass and a plasticizer of 10 to 30% by mass based on a solid content of the shell and the core contains a flavoring agent of 1 to 100% by mass based on a total amount of the core (claim 1). The shell of the spherical capsule is prepared by using a gelatin having a bloom value of at least 200, preferably 240 to 300 (claim 4 of Patent Literature 1). When a gelatin having such a high bloom as disclosed in Patent Literature 1 is employed for producing a capsule, it has been found that the capsule shell does not have sufficient solubility in the oral cavity.

JP H10-512141 A (Patent Literature 2) discloses a method for forming a micro-capsulated food or flavor capsule comprising providing food or flavor particles to be encapsulated; forming a mixture of hot-water fish gelatin and the above-mentioned food or flavor particles in aqueous medium; and micro-encapsulating the particles in the gelatin by a composite coacervation method at an elevated temperature to form a micro-capsulated capsule (claim 1). In this method, the fish gelatin preferably has a bloom value of about 150 to 300, preferably a bloom value of about 250 to 300 (claims 4 and 5). Patent Literature 2 also employs gelatin having high bloom values. The micro-capsule of Patent Literature 2 is obtained by composite coacervation method which is absolutely different from the process of the present invention.

CITATION LIST

Patent Literature

[PTL 1]
JP 2006-512944 A
[PTL 2]
JP H10-512141 A

SUMMARY OF INVENTION

Technical Problem

The present invention is to dissolve the above problem and is to provide a seamless capsule which easily dissolves in the oral cavity.

Solution to Problem

The present invention provides a seamless capsule comprising a capsule content solution, and a capsule shell enclosing the capsule content solution,
wherein the capsule shell comprises a gelatin having a bloom value of 50 to 190 and
wherein the seamless capsule has a capsule shell-dissolution time of 60 seconds or less when the dissolution time is determined by a disintegration test using water as a test solution.

The present invention also provides a seamless capsule, comprising a capsule content solution and a capsule shell enclosing the capsule content solution, obtained by pressing out the capsule content solution from a first nozzle and simultaneously extruding a preparation solution of the capsule shell from a second nozzle, using a multiple nozzle comprising a first nozzle and a second nozzle having concentrically increasing diameters, to form a composite jet, and then pouring the composite jet into a cooling solution, wherein
the multiple nozzle is composed of the first nozzle and the second nozzle concentrically disposed on the periphery of the first nozzle,
the preparation solution of the capsule shell comprises a gelatin having a bloom value of 50 to 190, water and ethanol, and
a mass ratio of water and ethanol is within the range of 40/60 to 95/5 in water/ethanol.

The capsule shell preferably contains a gelatin in an amount of 30 to 60% by mass based on a total mass of the capsule shell and further contains a polyhydric alcohol in an amount of 5 to 50% by mass based on a total mass of the capsule shell.

The capsule shell may further comprise a saccharide compound in an amount of 1 to 60% by mass based on a total mass of the capsule shell.

The seamless capsule preferably has a diameter of 0.3 to 10 mm and contains the capsule shell in an amount of 2 to 30% by mass based on a total amount of the seamless capsule.

The preparation solution of the capsule shell preferably contains a gelatin in an amount of 15 to 40% by mass.

The present invention further provides a process for producing a seamless capsule, comprising the following steps;

a step of simultaneously extruding both a solution of the capsule content solution from a first nozzle and a preparation solution of the capsule shell from a second nozzle to form a composite jet, using a multiple nozzle comprising a first nozzle and a second nozzle having concentrically increasing diameters, and a step of pouring the composite jet into a cooling solution, wherein the multiple nozzle is composed of the first nozzle and the second nozzle concentrically disposed on the periphery of the first nozzle, the preparation solution of the capsule shell comprises a gelatin having a bloom value of 50 to 190, water and ethanol, and a mass ratio of water and ethanol is within the range of 40/60 to 95/5 in water/ethanol.

In the above process, it is preferred that the preparation solution of the capsule shell contains a gelatin in an amount of 15 to 40% by mass based on a total amount of the capsule shell.

In the above process, it is preferred that the resulting capsule has a capsule shell-dissolution time of the capsule shell of 60 seconds or less when the dissolution time is determined by a disintegration test using water as a test solution.

The present invention also provides a seamless capsule obtainable by the above process for producing a seamless capsule.

Advantageous Effects of Invention

The seamless capsule of the present invention has a capsule shell-dissolution time of the capsule shell of 60 seconds or less when the dissolution time is determined by a disintegration test using water as a test solution and therefore easily dissolves in the oral cavity. The seamless capsule of the present invention has such a short dissolution time in water and the capsule shell would disappear rapidly and smoothly when one takes it in. The capsule does not bring unpleasant feeling because of remaining of the shell.

The seamless capsule of the present invention keeps the content safely even if the content is in the form of liquid or solution and is easily produced by a dropping method using a multiple nozzle. The seamless capsule of the present invention rapidly dissolves in the oral cavity. The seamless capsule of the present invention is compatible with both shape stability and capsule shell solubility, although the two properties are inconsistent with each other.

BRIEF DESCRIPTION OF DRAWINGS

FIG. 1 shows a schematic cross-section of a nozzle portion of an apparatus for producing a seamless capsule of the present invention.

DESCRIPTION OF EMBODIMENTS

Seamless Capsule

The seamless capsule of the present invention is explained by using the figure. A seamless capsule (10) in FIG. 1 is a schematic cross-section of one embodiment of the seamless capsule of the present invention. The seamless capsule (10) consists of a capsule shell (11) and a capsule content solution (12) which is enclosed in the capsule shell.

Capsule Shell

According to the present invention, the capsule shell comprises a gelatin having a bloom value of 50 to 190 as a main material for forming the capsule shell of the seamless capsule. The term "bloom value" used herein means strength of gel which is generally used as a standard indicating quality of gelatin and is determined by a measuring method called "bloom method" used world widely. The bloom value is determined according to JIS K 6503. Concretely, the bloom value is determined by loading a weight on a gelled gelatin prepared from 6.67% by mass of gelatin solution, using a plunger having a diameter of 12.7 mm, and deciding a load weight when a surface of the gelled gelatin is loaded down 4 mm.

In gelatin, the larger the bloom value, the higher the strength of gel, which satisfies strength necessary for producing a seamless capsule. On the other hand, smaller strength of gel is suitable for dissolubility in the oral cavity. For example, JP 2006-512944 A (Patent Literature 1) discloses in paragraph [0017] that a mixture of a gelatin having low bloom value and a gelatin having middle bloom value is known in order to improve solubility of capsule shell in the oral cavity. However, in the field of seamless capsules, a seamless capsule formed from a gelatin having a bloom value of less than 200 as a main material of capsule shell has not been considered. For an evidence of this, Patent Literature also states in paragraph [0019] that "it is not possible to attain suitable process stability in a capsule employing fish gelatin having a bloom value of less than 200 as gelatin solely employed in the capsule shell." If the capsule shell of the seamless capsule is prepared by general method using only gelatin having a bloom value of less than 200, the resulting shell does not have sufficient strength for processing and is not good.

According to the present invention, the capsule shell solely employs a gelatin having a bloom value of 50 to 190 which has not been solely used in the prior art. The capsule shell can be prepared from the above mentioned gelatin which is combined with water and ethanol to dissolve in a capsule preparation solution for the capsule shell.

The gelatin used for the present invention can preferably have a bloom value of 80 to 150, more preferably 100 to 140. Bloom values of more than 190 would lower solubility of the capsule shell of the resulting seamless capsule. Bloom values of less than 50 do not keep the capsule content solution The gelatin employed in the present invention is not limited as long as it has a bloom value of 50 to 190. The gelatin includes, for example, acid-processed gelatin (A type gelatin) or alkali-processed gelatin (B type gelatin) obtained from pig-origin gelatin (pig skin or pig bone gelatin), fish-origin gelatin (fish scale or fish skin gelatin), cattle-origin gelatin (cattle bone or cattle skin gelatin), and the like. In the above gelatin, preferred is A type gelatin. Fish-origin gelatin is preferably used in the present invention.

The gelatin preferably has a melting point of 26° C. or less, preferably within the range of 15 to 25° C., more preferably within the range of 19 to 24° C. The melting point of gelatin can be determined by glue and gelatin testing method according to JIS K 6503. More particularly, a gelatin solution of 10 mass % concentration is gelled in a glass tube having a diameter of 10 mm to form a gelled gelatin having 45 mm long starting from a position of 5 mm from the end. It is put in a water tank as the position of 5 mm from the end is down in the tank, and heated to melt the gelled gelatin.

Babbles present in the gel go up and an upper end of babbles goes up 10 mm at which a temperature is called a melting point of gelatin. Gelatin having a melting point of 19 to 24° C. includes, for example, fish-origin gelatin. The fish-origin gelatin has low content of imino acid, such as proline, hydroxy proline, and the like, in comparison with mammal-origin gelatin, such as pig-origin gelatin or cattle origin gelatin. The fish-origin gelatin has lower melting point in comparison with mammal-origin gelatin which generally has a melting point of 27 to 30° C.

Gelatin is contained in the capsule shell in an amount of 30 to 60% by mass, more preferably 35 to 55% by mass, most preferably 40 to 55% by mass, based on a total amount of the capsule shell.

The capsule shell of the seamless capsule of the present invention may contain water soluble polyhydric alcohol or a water soluble derivative thereof (hereinafter called as "polyhydric alcohol compound") in addition to gelatin. The polyhydric alcohol compound includes, for example, glycerin, polyglycerin, ethylene glycol, polyethylene glycol, propylene glycol, polypropylene glycol, ethylene oxide-propylene oxide copolymer, sugar ester, glyceride, sorbitan ester and the like. In these compounds, preferred is glycerin.

The polyhydric alcohol compound contained in the capsule shell can fast a dissolving speed in the oral cavity. It also enhances softness of the capsule shell. When the polyhydric alcohol compound is contained in the capsule shell, it is contained in an amount of 5 to 50% by mass, more preferably 10 to 45% by mass, most preferably 15 to 40% by mass, based on a total amount of the capsule shell.

The capsule shell may contain saccharide compound, if necessary, in addition to gelatin having a bloom value of 50 to 190. The saccharide compound includes, for example, monosaccharide, oligosaccharide, sugar alcohol, polysaccharide and the like. The monosaccharide includes, for example, glucose and the like. The oligosaccharide includes, for example, disaccharide, such as sucrose (cane sugar), lactulose, lactose, maltose, trehalose, cellobiose; a dehydro-condensate of disaccharide, such as raffinose, panose, maltotriose, melezitose, gentianose; and the like. The sugar alcohol includes, for example, sorbitol, mannitol, maltitol, erythritol, lactitol, xylitol and the like. Polysaccharide includes, for example, seaweed-origin polysaccharide, plant and plant seed-origin polysaccharide, microorganism-origin polysaccharide, starch, starch modified and the like. Examples of the seaweed-origin polysaccharides are alginic acid and its derivative, agar, carrageenan and the like. Examples of plant and plant seed-origin polysaccharides are pectin, glucomannan, gum arabic, gum tragacanth, gum karaya, guar gum, locust bean gum, tara gum, *psyllium* seed gum, and the like. Examples of microorganism-origin polysaccharides are xanthan gum, pullulan, gellan gum, curdlan and the like. Starch can be any starch generally employed. Starch modified includes hydrolyzed starch and the like. In the saccharide compound, preferred are sorbitol, mannitol, maltitol, erythritol, lactitol, xylitol, sucrose, trehalose, starch, starch modified and the like.

The saccharide compound contained in the capsule shell enhances strength of gel and also enhances film forming ability of the capsule shell. When saccharide compound is employed, it is contained in an amount of 1 to 60% by mass, preferably 5 to 40% by mass, more preferably 10 to 30% by mass, based on a total amount of the capsule shell.

The capsule shell may further contain colorant, taste component (sweetener, acidifier or bittering agent), antiseptic agent, flavor and the like, if necessary.

Capsule Content Solution

In the present invention, the content solution enclosed in the seamless capsule is not limited, but includes lipophilic or hydrophilic liquid substance, a suspension of the liquid substance and powder insoluble in the liquid substance or a mixture of the liquid substance. The content solution may contain lipophilic or hydrophilic components contained in functional food or function beverage, such as various vitamin, mineral, flavor, extract and the like. The hydrophilic liquid substance includes, for example, water (including purified water, ion exchanged water and the like), water soluble alcohol, polyhydric alcohol (glycerin, mannitol, sorbitol and the like), and a mixture thereof. The lipophilic liquid substance includes, for example, glycerin fatty acid ester, sucrose fatty acid ester, medium-chain fatty acid triglyceride (MCT), lauric acid, palmitic acid, stearic acid, myristic acid, oleic acid, behenic acid, vegetable fats and oils (palm oil, sunflower oil, safflower oil, sesame oil, rapeseed oil, grape seed oil and a mixture thereof) and a mixture thereof.

In the case where the capsule content solution is a suspension of lipophilic liquid substance and powder insoluble in the lipophilic liquid substance, the seamless capsule can be the two layer structure seamless capsule (10) as shown in FIG. 1, including the capsule content solution (12) and the capsule shell (11).

In the case where the capsule content solution is a suspension of hydrophilic liquid substance and powder insoluble in the hydrophilic liquid substance, the seamless capsule can be three layer structure seamless capsule including a capsule content solution, an intermediate layer isolating the capsule content solution from a capsule shell, and the capsule shell.

Seamless Capsule

The seamless capsule of the present invention has a capsule shell-dissolution time of 60 seconds or less when the dissolution time is determined by a disintegration test using water as a test solution, which is short period of time and easily dissolves in the oral cavity. The seamless capsule of the present invention has such a short dissolution time in water and the capsule shell would disappear rapidly and smoothly when one takes it in. The capsule does not bring unpleasant feeling because of remaining of the shell.

The dissolution time of the capsule shell by way of disintegration test is determined by a disintegration test (test solution: water) according to 16th revision Japanese Pharmacopoeia. Concretely, a capsule is put in water of 37° C. using a disintegration test apparatus described in "disintegration test method" of Japanese Pharmacopoeia. The apparatus is functioned and a time when the capsule disappears by eyes (any remaining material is not found by eyes) is determined as dissolution time.

A size of a seamless capsule and a sort of a capsule content solution are suitably selected according to usage and application. For example, the seamless capsule has a diameter of 0.3 to 10 mm, preferably 0.5 to 8 mm, more preferably 1 to 6 mm. An amount of the capsule shell is within the range of 2 to 30% by mass, preferably 5 to 20% by mass, based on a total amount of the seamless capsule.

The seamless capsule may have a thickness of the capsule shell of 10 to 150 μm, preferably 30 to 100 μm, more preferably 40 to 80 μm. The thickness of the shell of the above range would provide both good solubility and good maintaining properties of capsule content solution.

Method for producing capsule A method for producing the seamless capsule of the present invention is a method using a multiple nozzle (dripping method), which is disclosed in JP S58-22062 A and JP S59-131355 A.

In the method for producing capsules, a preparation solution of the capsule shell and a capsule content solution are preliminary prepared. The preparation solution of the capsule shell of the seamless capsule of the present invention is prepared by dispersing a gelatin having a 50 to 190 bloom value and optionally a polyhydric alcohol, saccharide compound and another additive in a medium. According to the present invention, the medium should be a mixture of water and ethanol and is specific to the present invention. Water can be purified water, ion-exchanged water and the like.

According to the present invention, the gelatin which is contained in the capsule shell for imparting good solubility in the oral cavity can be only a gelatin having 50 to 190 bloom value. In preparing conventional seamless capsules, gelatin having a bloom value of not less than 200 is generally employed. Gelatin having a bloom value of less than 200 has not solely been employed for producing the conventional seamless capsules. This is because sole use of the gelatin having a bloom value of less than 200 does not impart sufficient strength for the capsule shell in preparing the seamless capsule. In the production of the seamless capsule, the capsule shell has very low strength and is easily damaged or broken at the time of both immediate after dropping a preparation solution for capsule shell from a nozzle (as composite jet) and before solidifying the solution to form capsule shell. In order to avoid the damages in the condition of the composite jet, it has been necessary in the conventional technique to use gelatin having a bloom value of not less than 200.

The use of the gelatin having a bloom value of not less than 200, however, does not provide swift and good solubility in the oral cavity with the resulting seamless capsules. The present inventors tried to solely use gelatin having a bloom value of 50 to 190 as gelatin contained in capsule shell, to attain good solubility in the oral cavity. In order to use such gelatin, it was conducted that strength immediate after dropping it (the composite jet) from a nozzle was enhanced by reducing a water content and increasing gelatin content in the preparation solution of the seamless capsule. This method, however, increased viscosity of the preparation solution too much and did not form seamless capsules. Viscosity of the preparation solution is very important for producing seamless capsules, because seamless capsules are produced by a dropping method. If viscosity is not within suitable ranges, the composite jet would not form liquid drops and would not drop suitably and would continuously extrude as string.

In order to solve the above difficulty, the present inventors have intensely studied and experimented, and have found that the gelatin having a bloom value of 50 to 190 is mixed with a mixture of ethanol and water to form a preparation solution for a capsule shell of a seamless capsule, whereby viscosity of the preparation solution is kept suitable range to form seamless capsule by a dripping method and strength of the composite jet of the capsule is enhanced to form seamless capsules. This method makes it possible to keep sufficient strength in the form of composite jet solely using gelatin having a bloom value of 50 to 190 in a small content of water. A presence of ethanol in the preparation solution of the capsule shell also reduces viscosity significantly.

Ethanol generally has not employed for producing seamless capsules in the prior art when gelatin is used as main material for capsule shell. This is because ethanol generally modifies protein constituting gelatin and separates gelatin from liquid medium. For example, in a coacervation method (or phase separation method) which is one of methods for producing microcapsules, ethanol is added to a gelatin water solution to give rise to phase separation to form a coacervation. Accordingly, the coacervation method uses phenomenon that addition of ethanol separates gelatin from liquid medium.

In the present invention, gelatin having a bloom value of 50 to 190 is solely used and mixed with a mixture of water and ethanol to dissolve. A mass ratio of water and ethanol in the preparation solution for the capsule shell is preferably within the range of 40/60 to 95/5 (water/ethanol), more preferably within the range of 50/50 to 90/10. Mass ratios of the above range can produce a preparation solution of the capsule shell without separating gelatin having a bloom value of 50 to 190. Gelatin having a bloom value of 50 to 190 generally does not separate out even if ethanol is used within the above range, because the gelatin contains a small amount of α-chain.

In addition, an amount of ethanol contained in the preparation solution of the capsule shell can preferably be within the range of 5 to 60% by mass, more preferably 10 to 50% by mass, most preferably 20 to 40% by mass. In the present invention, the addition of ethanol in the preparation solution of the capsule shell can effectively inhibit propagation of microorganisms.

The preparation solution of the capsule shell of the present invention can preferably contain gelatin having a bloom value of 50 to 190 as main material for forming capsule shell in an amount of 15 to 40% by mass, based on a total mass of the preparation solution of the capsule shell. The amount of the gelatin can preferably be 18 to 35% by mass, more preferably 20 to 30% by mass. Amounts of more than 40% by mass increase viscosity of the preparation solution of the capsule shell and make it difficult to fatal a capsule. Those of less than 15% by mass reduce physical strength of the resulting capsule shell and make it impossible to use for seamless capsules.

The preparation solution of the capsule shell preferably has a viscosity of 30 to 350 mPa·s, more preferably 50 to 300 mPa·s, most preferably 100 to 250 mPa·s at 60° C. Viscosities within the above range make it possible to effectively produce seamless capsules by a dripping method.

The capsule content solution preferably has a viscosity of 20 to 350 mPa·s, more preferably 50 to 300 mPa·s, most preferably 100 to 250 mPa·s.

According to the present invention, one embodiment of the method for preparing the seamless capsule comprises providing a preparation solution of a capsule shell to a first nozzle (120) and providing a capsule content solution to a second nozzle (110), employing a double nozzle as shown in FIG. 1. Then, each solution is simultaneously extruded from each cyclic aperture of the nozzle to form a two layer composite jet and to pour it into a cooling solution which flows downwardly, followed by forming a seamless capsule (10).

The cooling solution has a temperature of 20° C. or less, preferably 1 to 18° C. Each solution extruded from each nozzle has a temperature of 15 to 70° C., preferably 20 to 65° C., although the temperature is not limited thereto.

The cooling solution includes, for example, medium-chain fatty acid triglyceride (MCT), plant fatty acid (palm oil, sunflower oil, safflower oil, sesame oil, rapeseed oil, grape seed oil and a mixture thereof), liquid paraffin and a mixture thereof.

In the method for producing the seamless capsule of the present invention, suitable vibration can be applied to the composite jet by using a vibration method to smoothly cut the composite jet, thus obtaining capsules having uniform capsule size. The above multiple nozzle can preferably be a concentric multiple nozzle.

In the case where the seamless capsule has three-layer structure, a liquid substance separating the capsule shell from the capsule content solution includes, for example, the above mentioned lipophilic liquid material. The liquid substance for separation may contain effective material, flavor and the like. In the case where a seamless capsule having three-layer structure is produced, the same nozzle can be used, with the exception that another nozzle is inserted inside the inner nozzle (120), to form a three layer nozzle. If necessary, a seamless capsule having a four layer structure can also be produced by using similar method.

The seamless capsule of the present invention may be rinsed with water, or heated or sterilized, according to its application. The capsule may also be dried by conventional drying method, to obtain heat resistant dried capsule. It should be noted that Examples described hereinafter contain an example which produces seamless capsules dried by conventional drying method. However, drying seamless capsules are not always necessary and, according to usage, shell containing much amount of water can be made if necessary. In the case where the capsule shell is wet, the capsule can take any shape, such as spherical, hemispherical, button shape or indeterminate shape.

In the present invention, as the preparation solution of the capsule shell contains both water and ethanol, a water content of the resulting seamless capsule is reduced and drying can be finished in a shorter period of time.

The seamless capsule obtained as mentioned above can easily dissolve in the oral cavity because the capsule shell contains gelatin having a bloom value of 50 to 190. The seamless capsule of the present invention has a capsule shell-dissolution time of the capsule shell of 60 seconds or less when the dissolution time is determined by a disintegration test using water as a test solution and therefore easily dissolves in the oral cavity. The seamless capsule of the present invention has such a short dissolution time in water and the capsule shell would disappear rapidly and smoothly when one takes it in. The capsule does not bring unpleasant feeling because of remaining of the shell.

EXAMPLES

The present invention is explained based on the following Examples which, however, are not construed as limiting the invention to their details. The terms "part" and "%" employed in Examples are based on mass, unless otherwise indicated.

Example 1

Seventy parts of medium-chain fatty acid triglyceride (MCT) and 10 parts of strawberry flavor were mixed to form a uniform solution, to which 20 parts of sucrose acetate isobutyrate (SAIB) was added and specific gravity and viscosity were adjusted to obtain a capsule content solution. It has a viscosity of 32 mPa·s (25° C.).

Twenty five parts of gelatin (130 bloom (strength of gel), available from Nippi Co., Ltd.), 15 parts by weight of glycerin, 10 parts of mannitol and 25 parts of purified water were uniformly mixed and dissolved at 60° C. Then, 25 parts of ethanol was added thereto and mixed until it becomes uniform, to obtain a preparation solution of a capsule shell. The preparation solution had a viscosity of 240 mPa·s (60° C.).

Next, using a seamless capsule producing apparatus (manufactured by Morishita Jintan Co., Ltd.) having a structure as shown in FIG. 1, the capsule content solution and the capsule shell preparation solution were simultaneously poured into a cooling oil of 10° C. from a second nozzle 110 regarding the capsule content solution and from a first nozzle 120 regarding the capsule shell preparation solution, to form seamless capsules having two layer structure. The formed capsules were airy dried at a temperature of 20 to 30° C. to evaporate water and ethanol in the capsule shell.

The resulting seamless capsules have a diameter of 5 mm and its shell amount ratio was 10% based on a total amount of the seamless capsule.

Comparative Example 1

Seamless capsules were produced as generally described in Example 1, with the exception that gelatin was changed to gelatin having a 280 bloom (available from Nippi Co., Ltd.).

Comparative Example 2

A capsule shell preparation solution was prepared as generally described in Example 1, with the exception that an amount of purified water was changed to 50 parts and ethanol was not used. The resultant capsule shell preparation solution had a viscosity of 180 mPa·s (60° C.).

Seamless capsules were tried to produce by using the above capsule shell preparation solution as generally described in Example 1, but seamless capsules were not produced because of extremely low gelation strength of the capsule shell preparation solution.

The seamless capsules obtained in Example 1 and Comparative Examples were subjected to the following evaluation. The results are shown in Table 1.

Determination of Capsule Shell-Dissolution Time

The dissolution time of the capsule shell of the seamless capsules is determined by a disintegration test (test solution: water) according to 16th revision Japanese Pharmacopoeia. The capsules were put in water of 37° C. using a disintegration test apparatus (NT-2 available from Toyama Sangyo Co., Ltd.) described in "disintegration test method" of Japanese Pharmacopoeia. The apparatus was functioned and a time when the capsule disappears by eyes (any remaining material was not found by eyes) was determined as dissolution time.

Evaluation of Intake of Seamless Capsules in the Oral Cavity

The seamless capsule was put in the oral cavity and left as it was to determine a time when one felt the capsule disappeared in the oral cavity. The evaluation was conducted five times and its average time was calculated.

Appearance Evaluation of Seamless Capsules

Appearance of the resultant seamless capsules was evaluated according to the following criteria:

Appearance Criteria

Good: They kept spherical shape and kept good shape.

Bad: They did not keep shape of seamless capsule.

TABLE 1

|  | Example number 1 | Comparative Example number 1 | Comparative Example number 2 |
| --- | --- | --- | --- |
| Bloom value (strength of gel) | 130 | 280 | 130 |
| Capsule shell dissolution time (seconds) | 58 | 96 | — |
| Evaluation of intake of seamless capsules in the oral cavity (seconds) | 18 ± 3 | 40 ± 5 | — |
| Appearance evaluation of seamless capsule | Good | Good | Bad |

The seamless capsules obtained in Example 1 had smaller capsule shell dissolution time and rapidly dissolved in the oral cavity. On the other hand, the seamless capsules of Comparative Example 1 had longer capsule shell dissolution time and did not easily dissolve in the oral cavity. In Comparative Example 2, seamless capsule were not obtained at all.

INDUSTRIAL APPLICABILITY

The seamless capsule of the present invention has a capsule shell-dissolution time of the capsule shell of 60 seconds or less when the dissolution time is determined by a disintegration test using water as a test solution and therefore easily dissolves in the oral cavity. The seamless capsule of the present invention keeps the content safely even if the content is in the form of content solution and is easily produced by a dropping method using a multiple nozzle. The seamless capsuled of the present invention rapidly dissolves in the oral cavity. The seamless capsule of the present invention is compatible with both shape stability and capsule shell solubility, although the two properties are inconsistent.

REFERENCE SIGNS LIST

10: Seamless capsule
11: Capsule shell
12: Capsule content solution
110: Second nozzle
120: First nozzle

The invention claimed is:

1. A process for producing a seamless capsule, comprising steps of;
   (i) using a coaxial nozzle comprising an inner nozzle and an outer nozzle having concentrically increasing diameters to simultaneously extrude both a capsule content solution from the inner nozzle and a preparation solution for the capsule shell from the outer nozzle to form a composite jet; and
   (ii) pouring the composite jet into a cooling solution,
   wherein the capsule content solution and the seamless capsule shell form a two layer structure,
   wherein the preparation solution for the capsule shell comprises gelatin having a bloom value of 50 to 190, water and ethanol, and
   wherein the mass ratio of water to ethanol is within the range of 40/60 to 95/5.

2. The process for producing a seamless capsule of claim 1, wherein the preparation solution of the capsule shell contains gelatin in an amount of 15 to 40% by mass based on the total amount of the capsule shell.

3. The process for producing a seamless capsule of claim 1, wherein the resulting capsule has a capsule shell-dissolution time of the capsule shell of 60 seconds or less when the dissolution time is determined by a disintegration test using water as a test solution.

* * * * *